United States Patent
Camporesi et al.

(10) Patent No.: US 10,827,967 B2
(45) Date of Patent: Nov. 10, 2020

(54) EMOTIONAL/BEHAVIOURAL/PSYCHOLOGICAL STATE ESTIMATION SYSTEM

(71) Applicant: Centro Studi S.r.l., Potenza (IT)

(72) Inventors: Alberto Camporesi, Potenza (IT); Vito Santarcangelo, Potenza (IT)

(73) Assignee: Centro Studi S.r.l., Potenza (IT)

( * ) Notice: Subject to any disclaimer, the term of this patent is extended or adjusted under 35 U.S.C. 154(b) by 305 days.

(21) Appl. No.: 15/764,695

(22) PCT Filed: Sep. 30, 2015

(86) PCT No.: PCT/EP2015/072639
§ 371 (c)(1),
(2) Date: Mar. 29, 2018

(87) PCT Pub. No.: WO2017/054871
PCT Pub. Date: Apr. 6, 2017

(65) Prior Publication Data
US 2018/0263545 A1    Sep. 20, 2018

(51) Int. Cl.
*A61B 5/16*        (2006.01)
*H04L 29/08*     (2006.01)
(Continued)

(52) U.S. Cl.
CPC ............ *A61B 5/165* (2013.01); *A61B 5/1114* (2013.01); *A61B 5/7267* (2013.01); *G06N 3/08* (2013.01);
(Continued)

(58) Field of Classification Search
CPC ......... A61B 5/163; A61B 5/165; A61B 5/167; A61B 5/168; A61B 5/1114; A61B 5/7264–7267
See application file for complete search history.

(56) References Cited

U.S. PATENT DOCUMENTS

2002/0169583 A1*  11/2002  Gutta ................. G08B 21/0423
                                                                702/188
2010/0066647 A1   3/2010  Tatsuta et al.
(Continued)

OTHER PUBLICATIONS

R.B. Miller, et al., "The New Strategic Selling—The Unique Sales System Proven Successful by the World's Best Companies", Grand Central Publishing, Apr. 2005, ISBN 9780446695190, pp. 65-78.
(Continued)

*Primary Examiner* — Thaddeus B Cox
(74) *Attorney, Agent, or Firm* — McCarter & English, LLP

(57) ABSTRACT

The present invention concerns a human emotional/behavioural/psychological state estimation system comprising a group of sensors and devices and a processing unit. The group of sensors and devices includes: a video-capture device; a skeletal and gesture recognition and tracking device; a microphone; a proximity sensor; a floor pressure sensor; user interface means; and one or more environmental sensors. The processing unit is configured to: acquire or receive a video stream captured by the video-capture device and data items provided by the skeletal and gesture recognition and tracking device, the microphone, the proximity sensor, the floor pressure sensor, the environmental sensor(s), and also data items indicative of interactions of a person under analysis with the user interface means; detect one or more facial expressions and a position of eye pupils, a body shape and features of voice and breath of the person under analysis; and estimate an emotional/behavioural/psychological state of the person on the basis of the acquired/received data items, of the detected facial expression(s), position of the eye pupils, body shape and features of the voice and the breath of the person, and of one or more predefined reference mathematical models modelling human emotional/behavioural/psychological states.

12 Claims, 1 Drawing Sheet

(51) Int. Cl.
 *A61B 5/00* (2006.01)
 *A61B 5/11* (2006.01)
 *G06N 3/08* (2006.01)
 G06N 5/02 (2006.01)
 G06N 7/00 (2006.01)

(52) U.S. Cl.
 CPC .............. *H04L 67/04* (2013.01); *H04L 67/12* (2013.01); *H04L 67/22* (2013.01); *A61B 5/163* (2017.08); *A61B 5/168* (2013.01); *G06N 5/022* (2013.01); *G06N 7/005* (2013.01)

(56) References Cited

U.S. PATENT DOCUMENTS

| | | |
|---|---|---|
| 2012/0116186 A1 | 5/2012 | Shrivastav et al. |
| 2013/0172693 A1* | 7/2013 | Ohana Lubelchick ............... G06F 19/3481 600/301 |
| 2014/0089399 A1 | 3/2014 | Chun et al. |
| 2014/0118225 A1 | 5/2014 | Jerauld |
| 2014/0280529 A1 | 9/2014 | Davis et al. |

OTHER PUBLICATIONS

PCT International Search Report and Written Opinion for PCT/EP2015/072639 dated Jun. 10, 2016.

\* cited by examiner

EMOTIONAL/BEHAVIOURAL/PSYCHOLOGICAL STATE ESTIMATION SYSTEM

CROSS-REFERENCE TO RELATED APPLICATIONS

This application is a 35 U.S.C. § 371 National Stage filing of International Application No. PCT/EP2015/072639, filed on Sep. 30, 2015.

TECHNICAL FIELD OF THE INVENTION

The present invention relates to a system for estimating an emotional and/or behavioural and/or psychological state of a person, such as a level of stress and/or anxiety and/or excitement, or, more in general, an emotional and/or behavioural and/or psychological state defined on the basis of sensed/measured/detected/computed parameters related to said person and of one or more predefined reference mathematical models modelling human emotional/behavioural/psychological states.

For example, the present invention can be advantageously, but not exclusively, exploited to detect (i.e., measure) and monitor levels of stress of workers who perform tasks that require high levels of concentration and that, in consequence, can induce a high level of stress, such as pilots of aircrafts and helicopters, drivers of rescue vehicles and trucks, machinery operators, controllers of workstations dedicated to plant safety, athletes, specialized technicians, etc.

Moreover, the present invention could be advantageously exploited also to detect emotional/behavioural/psychological states of people under indictment, lies of people under police interrogation, etc.

More in general, the present invention can be advantageously exploited in any sector in which it is felt the need to measure human emotional/behavioural/psychological state, thereby being applicable to many, extremely-different fields (such as also for clinical/medical researches, market/marketing researches, personnel selection, etc.).

STATE OF THE ART

Nowadays in many, extremely-different fields it is strongly felt the need to measure human emotional/behavioural/psychological state, for instance for safety or research purposes.

Accordingly, in the last years several emotional/behavioural/psychological state estimation systems and methods have been presented.

For example, US 2010/070456 A1 discloses an information processing system, that includes:
- a state estimation section that estimates a state of a user based on information including sensor information from at least one of
  - a behaviour sensor that measures a behaviour of the user,
  - a condition sensor that measures a condition of the user, and
  - an environment sensor that measures an environment of the user;
- a historical information storage section that stores state historical information about the user;
- a usualness level evaluation section that evaluates a usualness level of the user; and
- a write section that writes the usualness level of the user evaluated by the usualness level evaluation section in the historical information storage section, so that the usualness level is linked to each state of the user indicated by the state historical information about the user.

OBJECT AND SUMMARY OF THE INVENTION

An object of the present invention is that of providing an emotional/behavioural/psychological state estimation system having greater accuracy and reliability of estimation with respect to emotional/behavioural/psychological state estimation systems and methods currently known.

The aforesaid object is achieved by the present invention in that it relates to an emotional/behavioural/psychological state estimation system, as defined in the appended claims.

In particular, the system according to the present invention comprises a group of sensors and devices and a processing unit; wherein the group of sensors and devices includes:
- a video-capture device configured to capture a video stream of a person under analysis;
- a skeletal and gesture recognition and tracking device configured to provide data items indicative of gestures of a body of the person under analysis;
- a microphone configured to provide data items indicative of a voice of the person under analysis;
- a proximity sensor configured to provide data items indicative of a distance of the person under analysis;
- a floor pressure sensor configured to provide data items indicative of position and movements of feet of the person under analysis;
- user interface means, that comprise one or more input peripherals and one or more output peripherals, and that are designed to be used by the person under analysis;
and
- one or more environmental sensors configured to provide data items indicative of parameters related to an environment surrounding the person under analysis.

Moreover, the processing unit is configured to:
- acquire or receive the video stream captured by the video-capture device, the data items indicative of the gestures of the body of the person under analysis provided by the skeletal and gesture recognition and tracking device, the data items indicative of the voice of the person under analysis provided by the microphone, the data items indicative of the distance of the person under analysis provided by the proximity sensor, the data items indicative of the position and movements of the feet of the person under analysis provided by the floor pressure sensor, data items indicative of interactions of the person under analysis with the user interface means, and the data items indicative of the parameters related to the environment surrounding the person under analysis provided by the environmental sensor(s);
- detect one or more facial expressions and a position of eye pupils of the person under analysis on the basis of the acquired/received video stream;
- detect a body shape of the person under analysis on the basis of the acquired/received video stream and of the acquired/received data items indicative of the gestures of the body of said person;
- detect features of voice and breath of the person under analysis on the basis of the acquired/received data items indicative of the voice of said person; and estimate an emotional/behavioural/psychological state of the person under analysis on the basis of
the acquired/received data items,
the detected facial expression(s) of said person,
the detected position of the eye pupils of said person,
the detected body shape of said person,
the detected features of the voice and the breath of said person, and
one or more predefined reference mathematical models modelling human emotional/behavioural/psychological states.

BRIEF DESCRIPTION OF THE DRAWINGS

For a better understanding of the present invention, some preferred embodiments, provided only by way of non-limitative example, will be illustrated with reference to the attached drawings (not to scale), where.

DETAILED DESCRIPTION OF PREFERRED EMBODIMENTS OF THE INVENTION

The following description is provided to enable a person skilled in the art to implement and use the invention. Various modifications to the embodiments presented will be immediately evident to a person skilled in the art and the generic principles disclosed herein could be applied to other embodiments and applications without, however, departing from the scope of protection of the present invention, as defined in the appended claims.

Therefore, the present invention should not be intended as limited to the embodiments described and illustrated herein, but shall be given the broadest scope of protection consistent with the principles and characteristics described herein and defined in the appended claims.

Figure 1:
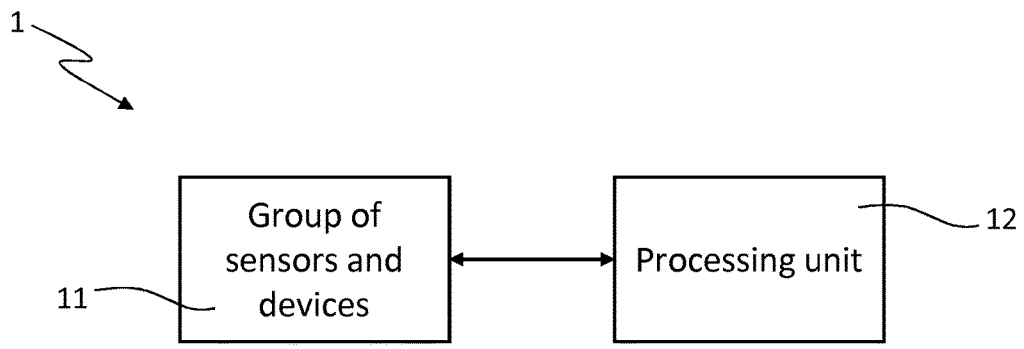
FIG. 1 schematically illustrates a general architecture of an emotional/behavioural/psychological state estimation system according to the present invention.

FIG. 1 schematically illustrates a general architecture of an emotional/behavioural/psychological state estimation system (denoted as a whole by 1) according to the present invention.

In particular, the system 1 includes:
a group of sensors and devices (denoted as a whole by 11) configured to provide data items related to a person under analysis (not shown in FIG. 1) (for example by carrying out operations of sensing and/or measuring and/or detecting and/or computing, etc.); and
a processing unit 12 designed to
acquire or receive the data items provided (i.e., sensed/measured/detected/computed) by the group of sensors and devices 11, and
process the acquired/received data items so as to estimate an emotional/behavioural/psychological state of the person under analysis on the basis of said data items.

Preferably, the processing unit 12 is further designed to control operation of the group of sensors and devices 11 by exchanging data therewith and sending commands thereto.

Conveniently, the processing unit 12 can be connected to the group of sensors and devices 11 in a wired and/or wireless fashion. In fact, different types of links can be advantageously used to connect the processing unit 12 to the group of sensors and devices 11, such as wired links, radio links based on Bluetooth technology or the so-called Near Field Communication (NFC) technology or any mobile phone technology, radio links based on networks of the LAN (Local Area Network), WAN (Wide Area Network), PAN (Personal Area Network) or BAN (Body Area Network) type, Internet-Protocol-based wired and/or wireless links, etc.

Conveniently, the processing unit 12 can be located close to the group of sensors and devices 11 and, thence, close to the person under analysis, or even attached to the body of the person under analysis (for example, said processing unit 12 could be attached to a belt or overalls worn by the person under analysis). The processing unit 12 could be also advantageously integrated into one and the same device with the group of sensors and devices 11 (such as a portable device, an interactive multimedia totem, a game machine, etc.), or located in one and same room or building along with the sensors and devices 11, or even remotely connected to the group of sensors and devices 11 and, hence, be far away from them and from the person under analysis.

Preferably, the emotional/behavioural/psychological state estimation is carried out by the processing unit 12 in real time. However, the emotional/behavioural/psychological state estimation could also be carried out not in real time and, thence, the processing unit 12 could also be not connected to the group of sensors and devices 11. In fact, in this latter case, the data items provided (i.e., sensed/measured/detected/computed) by the group of sensors and devices 11 could be stored on a portable data storage device (such as a USE flash drive, an external USB hard disk drive, etc.) to be, afterward, loaded on, and then processed by, the processing unit 12.

Conveniently, the processing unit 12 can be an electronic processing device specifically designed and programmed for, and completely dedicated to, human emotional/behavioural/psychological state estimation. Otherwise, the human emotional/behavioural/psychological state estimation carried out by the processing unit 12 (that will be described in detail in the following) can be also advantageously carried out by means of a correspondingly programmed computing device or system (such as a computer, a laptop, a server, a tablet, a smartphone, etc.) of the general purpose type, or dedicated also to other tasks.

Figure 2:
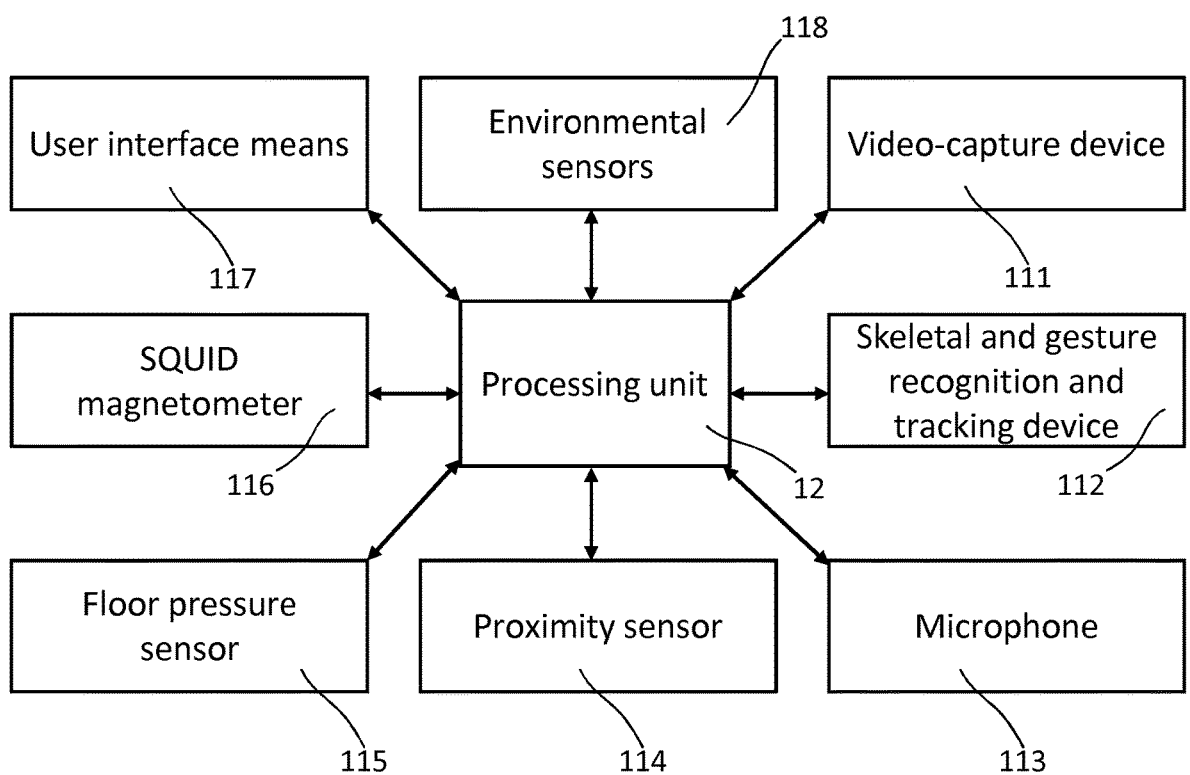
FIG. 2 schematically illustrates a preferred embodiment of the present invention.

FIG. 2 schematically illustrates a preferred embodiment of the present invention, wherein the group of sensors and devices 11 includes:
a video-capture device 111 configured to capture a video stream of the person under analysis (not shown in FIG. 2), said video stream comprising a sequence of images in colour or in greyscale;
a skeletal and gesture recognition and tracking device 112 configured to
detect and track gestures of the body of the person under analysis (for example by means of one or more cameras and processing means programmed to process video data from said camera(s) by implementing one or more skeletal and gesture recognition and tracking techniques), and
provide data items indicative of the gestures of the body of the person under analysis;
a microphone 113 configured to provide data items indicative of the voice of the person under analysis;
a proximity sensor 114, preferably an ultrasonic or passive infrared (PIR) sensor, configured to detect a distance of the person under analysis and to provide data items indicative of said distance;

a floor pressure sensor 115 configured to detect position and movements of the feet of the person under analysis and to provide data items indicative of said position and movements;

a magnetometer of the SQUID type (i.e., superconducting quantum interference device) 116;

user interface means 117 comprising one or more input peripherals (such as a keyboard and/or a keypad and/or a mouse and/o a joystick and/or a touch screen, etc.) and one or more output peripherals (such as one or more displays and/or touch screens) designed to be used by the person under analysis; and one or more environmental sensors 118 configured to measure parameters related to an environment surrounding the person under analysis (such as temperature, humidity, brightness, etc.) and to provide data items indicative of said parameters.

The processing unit 12 is configured to:

acquire/receive the video stream captured by the video-capture device 111, the data items indicative of the gestures of the body of the person under analysis provided by the skeletal and gesture recognition and tracking device 112, the data items indicative of the voice of the person under analysis provided by the microphone 113, the data items indicative of the distance of the person under analysis provided by the proximity sensor 114, the data items indicative of the position and movements of the feet of the person under analysis provided by the floor pressure sensor 115, the data items provided by the SQUID magnetometer 116, data items indicative of features of interaction of the person under analysis with the user interface means 117 (such as interaction speed), and the data items indicative of the parameters related to the environment surrounding the person under analysis provided by the environmental sensor(s) 118;

process the acquired/received video stream by implementing one or more human facial expression detection techniques, thereby detecting one or more facial expressions and a position of eye pupils of the person under analysis;

detect a shape of the body of the person under analysis on the basis of the acquired/received video stream and of the acquired/received data items indicative of the gestures of the body of said person, and conveniently also on the basis of the acquired/received data items indicative of the position and movements of the feet of said person;

detect features of voice and breath of the person under analysis (such as tone of voice, type of breath, breath frequency and intensity, etc.) on the basis of the acquired/received data items indicative of the voice of said person; and estimate an emotional/behavioural/psychological state of the person under analysis on the basis of
the acquired/received data items,
the detected facial expression(s) of said person,
the detected position of the eye pupils of said person,
the detected shape of the body of said person,
the detected features of the voice and the breath of said person, and
one or more predefined reference mathematical models modelling human emotional/behavioural/psychological states.

Preferably, the video stream captured by the video-capture device 111 is a colour video stream and the processing unit 12 can be further configured to:

detect one or more colours of clothes of the person under analysis on the basis of the acquired/received video stream; and estimate the emotional/behavioural/psychological state of said person also on the basis of the detected colour(s) of the clothes of said person.

Alternatively, the group of sensors and devices 11 can conveniently include one or more colour sensors configured to detect the colour(s) of the clothes of said person and to provide data items indicative of said colour(s). In this case, the processing unit 12 is configured to acquire/receive the data items indicative of the colour(s) of the clothes of the person under analysis provided by the colour sensor(s), and to estimate the emotional/behavioural/psychological state of said person also on the basis of said colour-related data items acquired/received.

The use of many data items, parameters and features of different types provided by the group of sensors and devices 11 and detected by the processing unit 12 results in an improvement in the accuracy and reliability of the emotional/behavioural/psychological state estimation performed by said processing unit 12 with respect to emotional/behavioural/psychological state estimation systems and methods currently known, such as the system according to US 2010/070456 A1.

In particular, the combined use of the data items related to the gestures of the body of the person under analysis provided by the skeletal and gesture recognition and tracking device 112, of the facial expression(s), the position of the eye pupils and the shape of the body of said person detected by the processing unit 12, and of the data items indicative of the parameters related to the surrounding environment provided by the environmental sensor(s) 118 allows to dramatically improve the accuracy and reliability of the emotional/behavioural/psychological state estimation performed by said processing unit 12, since in this way said estimation takes into consideration the overall human body language along with the respective environmental factors.

Therefore, the more different data items, parameters and features are sensed/measured/detected/computed by the group of sensors and devices 11 and/or detected/computed by the processing unit 12, the more accurate and reliable the emotional/behavioural/psychological state estimation performed by said processing unit 12 becomes.

Accordingly, the group of sensors and devices 11 could conveniently include also sensors and devices configured to measure physiological parameters of the person under analysis (such as blood pressure, heartbeat and heart rate, skin perspiration, presence of cortisol in saliva, pupil diameter, body temperature, etc.) and to provide data items indicative of the physiological parameters measured; the processing unit 12 could, thence, be conveniently configured to acquire/receive also, and to base the emotional/behavioural/psychological state estimation also on, said data items indicative of said measured physiological parameters of the person under analysis.

Furthermore, the processing unit 12 could be conveniently configured to base the emotional/behavioural/psychological state estimation also on additional data items indicative of gender and age of the person under analysis (for example, the processing unit 12 could be configured to obtain said additional data items directly from the person under analysis by means of the user interface means 117, or, as for the gender, the processing unit 12 could be configured to automatically detect the gender of the person under analysis on the basis of the acquired/received video stream).

Moreover, further information items advantageously exploitable by the processing unit 12 to perform the emotional/behavioural/psychological state estimation could be conveniently retrieved by said processing unit 12 also from other systems used by the person under analysis, such as social networks, banking systems, commercial databases, etc.

As for the predefined reference mathematical model(s) used by the processing unit 12 to estimate the emotional/behavioural/psychological state of the person under analysis, said predefined reference mathematical model(s) preferably comprise(s) one or more neuro-linguistic programming (NLP) models.

In particular, as is known, NLP models define several response modes, or behavioural states, of a person/interlocutor, such as those ones defined in R. B. Miller et al. *"The New Strategic Selling—The Unique Sales System Proven Successful by the World's Best Companies"* (Grand Central Publishing, April 2005, ISBN 9780446695190) which include:
- a "Growth" response mode (or behavioural state), in which a person/interlocutor is always ready to say yes in order to obtain a better thing introducing a "discrepancy" to be filled, with a consequent high probability of success in a sale/interaction involving said person/interlocutor;
- a "Trouble" response mode (or behavioural state), in which there is a defeat to be solved in the immediate future, with a consequent high probability of success in the sale/interaction;
- an "Even Keel" response mode (or behavioural state), in which there is no "discrepancy" to be filled, with a consequent low probability of success in the sale/interaction; and
- an "Overconfident" response mode (or behavioural state), in which the person/interlocutor is convinced of having more than what said person/interlocutor actually has, with a consequent nonexistent probability of success in the sale/interaction.

The capability to determine the behavioural state of a person/interlocutor at a given time and to monitor time variation of the behavioural state of said person/interlocutor represents a very important tool in order to better address communication and to foresee the relevant probability of success in an interaction (such as a sale) involving said person/interlocutor.

Therefore, the predefined reference mathematical model(s) used by the processing unit 12 to estimate the emotional/behavioural/psychological state of the person under analysis preferably comprise(s) one or more NLP models expanding the aforesaid four known response modes by introducing two states for each response mode, namely:
- a "Rational" state, in which the person/interlocutor has a definite perception; and
- a "Non-rational" state, in which the person/interlocutor has not a definite perception.

Accordingly, the NLP model(s) used by the processing unit 12 to estimate the emotional/behavioural/psychological state of the person under analysis preferably define(s) eight response modes, or behavioural states, namely: a "Rational Growth" response mode (or behavioural state), a "Non-rational Growth" response mode (or behavioural state), a "Rational Trouble" response mode (or behavioural state), a "Non-rational Trouble" response mode (or behavioural state), a "Rational Even Keel" response mode (or behavioural state), a "Non-rational Even Keel" response mode (or behavioural state), a "Rational Overconfident" response mode (or behavioural state), and a "Non-rational Overconfident" response mode (or behavioural state).

Therefore, in this way the system 1, by estimating the emotional/behavioural/psychological state of the person under analysis on the basis of the aforesaid eight response modes (i.e., "Rational Growth", "Non-rational Growth", "Rational Trouble", "Non-rational Trouble", "Rational Even Keel", "Non-rational Even Keel", "Rational Overconfident" and "Non-rational Overconfident") enables to foresee the probability of success in an interaction involving said person under analysis (for example for marketing/selling purposes).

Again preferably, said predefined reference mathematical model(s) used by the processing unit 12 to estimate the emotional/behavioural/psychological state of the person under analysis can comprise (also) one or more colour psychology models and/or one or more semantic network models.

According to a first specific preferred embodiment of the present invention, the processing unit 12 is configured to:
- compute, on the basis of the predefined reference mathematical model(s), synthesis values that synthetically indicate the acquired/received data items, the detected facial expression(s), the detected position of the eye pupils, the detected shape of the body, the detected features of the voice and the breath of the person under analysis (and preferably also the colour(s) of the clothes of said person);
- store reference values computed on the basis of the predefined reference mathematical model(s) and indicative of several different human emotional/behavioural/psychological states; and
- estimate the emotional/behavioural/psychological state of the person under analysis by comparing one or more of the computed synthesis values with the stored reference values.

More preferably, the processing unit 12 is configured to compute the synthesis values by:
- computing, on the basis of the predefined reference mathematical model(s), first synthesis values $A_1$, $A_2$, $A_3$, ..., $A_{N-1}$, $A_N$ each of which synthetically indicates a respective one among, or a respective subset of, the acquired/received data items, the detected facial expression(s), the detected position of the eye pupils, the detected shape of the body, the detected features of the voice and the breath of the person under analysis (and, preferably also the colour(s) of the clothes of said person);
- for each of the first synthesis values $A_1$, $A_2$, $A_3$, ..., $A_{N-1}$, $A_N$ computed, computing a corresponding second synthesis value according to the following mathematical formula $$B_i = 1 - \frac{A_i}{A_i^{MAX}},$$

where $A_i$ denotes a generic first synthesis value among $A_1$, $A_2$, $A_3$, ..., $A_{N-1}$, $A_N$, $B_i$ denotes the corresponding second synthesis value, and $A_i^{MAX}$ denotes the maximum value for $A_i$ according to the predefined reference mathematical model(s); and
- computing an overall synthesis value according to the following mathematical formula $$C = \frac{\sum_{i=1}^{N}(\gamma_i)^2 \cdot B_i}{\sum_{i=1}^{N}(\gamma_i)^2},$$

where $\gamma_i$ denotes a weighting factor related to the generic second synthesis value $B_i$ and computed on the basis of the predefined reference mathematical model(s), and where $0<\gamma_i \leq 1$.

Accordingly, the processing unit 12 is configured to estimate the emotional/behavioural/psychological state of the person under analysis by comparing the computed overall synthesis value with the stored reference values, which are, conveniently, reference thresholds computed on the basis of the predefined reference mathematical model(s).

According to a second specific preferred embodiment of the present invention, the processing unit 12 comprises a classifier trained to estimate the emotional/behavioural/psychological state of the person under analysis on the basis of:
the acquired/received data items;
the detected facial expression(s) of said person;
the detected position of the eye pupils of said person;
the detected shape of the body of said person;
the detected features of the voice and the breath of said person; and
the predefined reference mathematical model(s) modelling human emotional/behavioural/psychological states.

More preferably, said classifier comprises one or more artificial neural networks trained, during a preliminary phase known as "training phase", so as to have a transfer function that correlates
the acquired/received data items, the detected facial expression(s), the detected position of the eye pupils, the detected shape of the body, the detected features of the voice and the breath of the person under analysis (and preferably also the colour(s) of the clothes of said person)
with the emotional/behavioural/psychological state of said person
according to the predefined reference mathematical model(s) modelling human emotional/behavioural/psychological states.

Conveniently, the emotional/behavioural/psychological state estimations according to the aforesaid first and second specific preferred embodiments of the present invention could be also advantageously combined to further improve accuracy and reliability of estimation.

The advantages of the present invention can be immediately appreciated from the foregoing description.

In particular, it is worth noting that the present invention presents the following technical advantages:
the human emotional/behavioural/psychological state estimation according to the present invention is very accurate and reliable and can be performed in real time;
the person under analysis has total freedom of movement and is not restricted; and
the system according to the present invention can be specifically calibrated for each person and for each specific application environment (i.e., high adaptability and flexibility of the system).

It is important to underline that the present invention can be advantageously exploited in any sector in which it is felt the need to measure human emotional/behavioural/psychological state, thereby being applicable to many, extremely-different fields.

In particular, the present invention can be advantageously, but not exclusively, exploited for:
detecting and monitoring the level of stress of workers who perform tasks that require high levels of concentration and that, in consequence, can induce a high level of stress (such as pilots of aircrafts and helicopters, drivers of rescue vehicles and trucks, machinery operators, controllers of workstations dedicated to plant safety, athletes, specialized technicians, etc.);
detecting emotional/behavioural/psychological states of people under indictment, lies of people under police interrogation, etc.;
clinical/medical researches;
market/marketing researches; and also
personnel selection.

Finally, it is apparent that various modifications can be made to the present invention without departing from the scope of protection as defined in the appended claims.

The invention claimed is:
1. Emotional/behavioral/psychological state estimation system comprising a group of sensors and devices and a computing device, wherein the group of sensors and devices includes:
a video camera configured to capture a video stream of a person under analysis;
a skeletal and gesture recognition tracker configured to provide data items indicative of gestures of a body of the person under analysis;
a microphone configured to provide data items indicative of a voice of the person under analysis;
a proximity sensor configured to provide data items indicative of a distance of the person under analysis;
a floor pressure sensor configured to provide data items indicative of position and movements of feet of the person under analysis;
an user interface including one or more input peripherals and one or more output peripherals, the user interface designed to be used by the person under analysis; and
one or more environmental sensors configured to provide data items indicative of parameters related to an environment surrounding the person under analysis;
and wherein the computing device is configured to:
acquire or receive the video stream captured by the video camera, the data items indicative of the gestures of the body of the person under analysis provided by the skeletal and gesture recognition tracker, the data items indicative of the voice of the person under analysis provided by the microphone, the data items indicative of the distance of the person under analysis provided by the proximity sensor, the data items indicative of the position and movements of the feet of the person under analysis provided by the floor pressure sensor, data items indicative of interactions of the person under analysis provided by the user interface, and the data items indicative of the parameters related to the environment surrounding the person under analysis provided by the environmental sensor(s);
detect one or more facial expressions and a position of eye pupils of the person under analysis on the basis of the acquired/received video stream;
detect a body shape of the person under analysis on the basis of the acquired/received video stream and the acquired/received data items indicative of the gestures of the body of said person;

detect features of voice and breath of the person under analysis on the basis of the acquired/received data items indicative of the voice of said person; and estimate an emotional/behavioral/psychological state of the person under analysis on the basis of the acquired/received data items, the detected facial expression(s) of said person, the detected position of the eye pupils of said person, the detected body shape of said person, the detected features of the voice and the breath of said person, and one or more predefined reference mathematical models modelling human emotional/behavioral/psychological states wherein said predefined reference mathematical model(s) comprise(s) one or more neuro-linguistic programming models that is/are such that to model human emotional, behavioral or psychological states according to the following response modes: a "Rational Growth" response mode, a "Non-rational Growth" response mode, a "Rational Trouble" response mode, a "Non-rational Trouble" response mode, a "Rational Even Keel" response mode, a "Non-Rational Even Keel" response mode, a "Rational Overconfident" response mode, and a "Non-rational Overconfident" response mode.

2. The system of claim 1, wherein the group of sensors and devices further includes a SQUID magnetometer; and wherein the computing device is configured to estimate the emotional/behavioral/psychological state of the person under analysis also on the basis of data items provided by said SQUID magnetometer.

3. The system according to claim 1, wherein the group of sensors and devices further includes sensors and devices configured to provide data items indicative of physiological parameters of the person under analysis; and wherein the computing device is configured to acquire or receive also said data items indicative of the physiological parameters and to estimate the emotional/behavioral/psychological state of the person under analysis also on the basis of said data items indicative of the physiological parameters.

4. The system according to claim 1, wherein the computing device is configured to estimate the emotional/behavioral/psychological state of the person under analysis also on the basis of additional data items indicative of gender and age of said person.

5. The system according to claim 1, wherein the computing device is configured to estimate the emotional/behavioral/psychological state of the person under analysis also on the basis of information items retrieved from other systems used by said person; and wherein said other systems used by the person under analysis include one or more of following systems: social networks, banking systems, commercial databases.

6. The system according to claim 1, wherein said predefined reference mathematical model(s) comprise(s) one or more semantic network models.

7. The system according to claim 1, wherein the computing device is configured to estimate the emotional/behavioral/psychological state of the person under analysis also on the basis of one or more colors of clothes of said person; and wherein said predefined reference mathematical model(s) comprise(s) one or more color psychology models.

8. The system of claim 7, wherein the video camera is configured to capture a color video stream of the person under analysis; and wherein the computing device is further configured to detect said one or more colors of the clothes of the person under analysis on the basis of the acquired/received color video stream.

9. The system of claim 7, wherein the group of sensors and devices further includes one or more color sensors configured to detect said one or more colors of the clothes of the person under analysis and to provide data items indicative of the detected color(s); and wherein the computing device is configured to acquire or receive also the data items indicative of the detected color(s) of the clothes of the person under analysis provided by the color sensor(s).

10. The system according to claim 1, wherein the computing device is configured to:

compute, on the basis of the predefined reference mathematical model(s), synthesis values that synthetically indicate the acquired/received data items, the detected facial expression(s) of the person under analysis, the detected position of the eye pupils of said person, the detected body shape of said person, the detected features of the voice and the breath of said person;

store reference values computed on the basis of the predefined reference mathematical model(s) and indicative of several different human emotional/behavioral/psychological states; and estimate the emotional/behavioral/psychological state of the person under analysis by comparing one or more of the computed synthesis values with the stored reference values.

11. The system according to claim 1, wherein the computing device is configured to execute a classifier trained to estimate the emotional/behavioral/psychological state of the person under analysis on the basis of:

the acquired/received data items;

the detected facial expression(s) of said person;

the detected position of the eye pupils of said person;

the detected shape of the body of said person;

the detected features of the voice and the breath of said person; and the predefined reference mathematical model(s) modelling human emotional/behavioral/psychological states.

12. The system of claim 11, wherein the classifier comprises one or more artificial neural networks.

\* \* \* \* \*